United States Patent [19]

Costanzi et al.

[11] 4,393,218

[45] Jul. 12, 1983

[54] 2,2,4,5,5-PENTAMETHYL-3-FORMYL-Δ³-PYRROLINE AND THE PREPARATION THEREOF

[75] Inventors: Silvestro Costanzi, S. Guiliano Mi; Francesco Tessarolo, Monza; Maurizio Brunelli, Milan, all of Italy

[73] Assignee: Anic, S.p.A., Palermo, Italy

[21] Appl. No.: 327,753

[22] Filed: Dec. 7, 1981

Related U.S. Application Data

[63] Continuation-in-part of Ser. No. 149,511, May 13, 1980, abandoned.

[30] Foreign Application Priority Data

May 29, 1979 [IT] Italy ............................ 23080 A/79

[51] Int. Cl.³ .......................................... C07D 207/24
[52] U.S. Cl. ................................... 548/530; 548/518

[58] Field of Search .................... 260/326.55; 548/530

[56] References Cited

PUBLICATIONS

Gensler et al., J. Organic Chem., vol. 43, pp. 4081–4085 (1978).

*Primary Examiner*—Mark L. Berch
*Assistant Examiner*—D. Springer
*Attorney, Agent, or Firm*—Morgan, Finnegan, Pine, Foley & Lee

[57] ABSTRACT

A process for preparing 2,2-dialkyl-4-methyl-5,5-dialkyl-3-formyl-Δ³-pyrrolines by reacting the corresponding dialkyl substituted di-tert-propargylamines with water at a pH equal to or less than 3.0. Preferably, an inorganic mercury compound is used as a catalyst.

3 Claims, No Drawings

2,2,4,5,5-PENTAMETHYL-3-FORMYL-Δ³-PYRROLINE AND THE PREPARATION THEREOF

The present application is a continuation-in-part of application Ser. No. 149,511 filed May 13, 1980, abandoned.

This invention relates to a process for preparing 2,2-dialkyl-4-methyl-5,5-dialkyl-3-formyl-Δ³-pyrroline, consisting of reacting di-tert-propargylamines with water at a pH equal to or less than 3, possibly in the presence of a mercury-based catalyst.

Nonconjugated acetylene and diacetylene compounds are known to react with water in the presence of mercury oxide in an acid environment, with the addition and formation of the corresponding carbonyl compound, i.e., aldehyde or ketone.

Thus, in the presence of HgO/H₂SO₄, acetylene forms acetaldehyde, propargyl alcohol forms 1-hydroxy-acetone in an acid environment in the presence of mercury salts, and methylbutynol forms 1,1-dimethyl-1-hydroxy-acetone with the same catalyst (Kirk and Othmer, Encyclopedia of Chemical Technology, 3rd edition, volume 1, pages 195, 247, 265), whereas diacetylene compounds, on hydration in the presence of mercury salts in an acid environment, form the corresponding dicarbonyl compounds (Thomas F. Rutledge, Acetylenes and Allenes, published by Reinhold, page 128; W. J. Gensler et al, Journal of Organic Chemistry, volume 43, 1978, page 4081). Even without metal catalysts, the reaction of compounds containing triple bonds with water in an environment made strongly acid by sulphuric acid (concentration 60–80%) leads to the formation of carbonyl compounds. (T. F. Rutledge, Acetylenes and Allenes, page 125).

It has now been surprisingly found that di-tert-propargylamines do not add two molecules of water in order to form the corresponding diketones, as would be expected, but instead also undergo a cyclizing reaction, to add only one molecule of water and form pentaalkyl-formyl-pyrrolines, which are heterocyclic products useful as intermediates for organic synthesis, in particular for the preparation of anti U.V. additives. The reaction takes place in accordance with the scheme

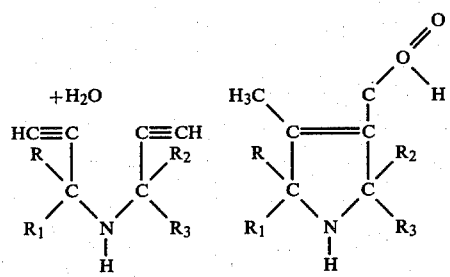

instead of the expected scheme:

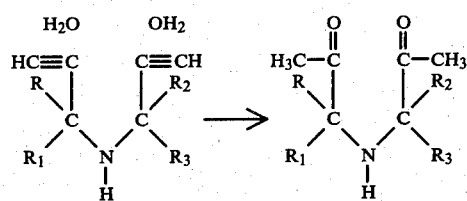

(R, R₁, R₂ and R₃ represent alkyl radicls as hereinafter defined).

The novel compounds of the present invention have the following structural formula:

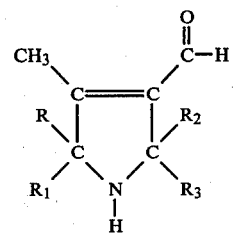

wherein R, R₁, R₂ and R₃ represent alkyl radicals having from 1 to 4 carbon atoms which can be the same as or different from each other.

The reaction takes place at low pH, preferably at a pH equal to or less than 3.

It has been therefore been found advantageous to operate under sulphuric acid acidity conditions sufficient to favor the reactions involved.

It has also been confirmed that the acid has its own catalytic function, which at low concentrations is synergistic to that of the catalyst when used.

The catalyst is constituted by an inorganic mercury compound. It has been found advantageous to use mercury oxide.

It has also been found that the best operating conditions for the purposes of the hydration/cyclization reaction in the presence of a catalyst are given by a sulphuric acid concentration of 45–50% of the total solution, and a mercury oxide content of about 5–10% by weight of the propargylamine to be converted, corresponding to about 0.3–0.6% of the total solution.

Thus, by operating under relatively moderate temperature conditions (between 100° and 115° C.) and an economically acceptable reaction time, a sufficiently advantageous reaction yield can be obtained. It has been found that, when the reaction is carried out at a temperature below 100° C., extremely low yields are obtained. If a catalyst is not used, the most favorable conditions are determined by a sulphuric acid concentration of 60–80% of the total solution, operating at a slightly higher temperature, preferably between 120° and 130° C.

Reaction tests are described hereinafter, by way of example, for the production of 2,2,4,5,5-pentamethyl-3-formyl-Δ³-pyrroline, in comparison with tests carried out without a catalyst and with a deficiency of sulphuric acid.

Subsequently, in order to confirm the structure of the product obtained, an in order to verify its further reactivity and consequent usability, it was hydrogenated in two successive stages, to give a product containing a functional —OH group, which could be further reacted, and thus act as a precursor for new useful products as hereinafter described.

EXAMPLE 1

200 cc of 96% H₂SO₄, 200 cc of H₂O, 3 g of HgO and 30 g of di-tert-propargyl-amine of formula:

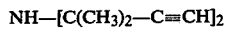

NH—[C(CH₃)₂—C≡CH]₂ were placed at an ambient temperature in a four neck flask fitted with a stirrer, thermometer and dropping funnel.

After the addition, the reaction mixture was heated to 110° C., and kept stirring for three hours at this temperature.

Decolorizing carbon was then added to the reaction mixture, which was then cooled by pouring it over ice, and filtered.

The filtrate was alkalized with a 40% solution of NaOH, and then extracted three times with ether.

The ether extracts were combined, dried over $MgSO_4$ and evaporated. The reaction product remained as a crude solid residue, which could be purified by crystallizing from petroleum ether (fraction 40°–60° C.).

The purified product was in the form of a yellow solid which melted at 69°–70° C., and which was identified by IR, NMR and Mass examination as 2,2,4,5,5-pentamethyl-3-formyl-$\Delta^3$-pyrroline.

EXAMPLE 2

220 cc of 98% sulphuric acid, 140 cc of water and 50 g of di-ter-propargyl-amine as used in example 1 were placed at ambient temperature in a four neck flask equipped as in example 1 (resultant sulphuric acid concentration 60%).

After the addition, the reaction mixture was heated under reflux to 125°–130° C. for one and a half hours, during which time the reaction kinetics were followed by a gas chromatograph.

The reaction mixture was then cooled, poured over ice, alkalized and extracted three times with ether.

The combined ether extracts were dried over magnesium sulphate and evaporated.

The solid residue was recyrstallized from petroleum ether (fraction 40°–60° C.) to give a crystalline solid with a yield of 40–60%, which on IR, NMR and Mass examination was found to be 2,2,4,5,5-pentamethyl-3-formyl-$\Delta^3$-pyrroline.

EXAMPLE 3

200 cc of 96% $H_2SO_4$, 200 cc of $H_2O$ and 30 g of di-tert-propargylamine were placed at ambient temperature in a four neck flask equipped as in example 1. The reaction mixture was heated to a temperature of 110° C. for three hours, and was then treated as in example 1.

The product recovered after removing the extraction solvent consisted of 90% of di-tert-propargyl-amine and 10% of 2,2,4,5,5-pentamethyl-3-formyl-3-pyrroline.

EXAMPLE 4

125 cc of 96% $H_2SO_4$, 3 g of HgO, 275 cc of $H_2O$ and 30 g of di-tert-propargyl-amine were placed at ambient temperature in a four neck flask fitted with a thermometer, dropping funnel, condenser and stirrer.

The reaction mixture was kept at 100° C. for four hours, and then treated as in the previous examples.

The product recovered after removing the extraction solvent consisted partly of the starting substance and of about 40% of 2,2,4,5,5-pentamethyl-3-formyl-$\Delta^3$-pyrroline.

EXAMPLE 5

Preparation of 2,2,4,5,5-pentamethyl-3-formyl-pyrrolidone. 20 g of pyrroline prepared as in example 1 were placed in an autoclave together with 50 cc of $CH_3OH$ and 2 g of Pd/C. The reaction mixture was left sitrring at ambient temperature under a pressure of 5 $kg/cm^2$ of $H_2$.

When no further $H_2$ absorption by the reaction mixture was observed, the catalyst was removed by filtration, and the said product was recovered by distillation.

The 2,2,4,5,5-pentamethyl-3-formyl-pyrrolidine was in the form of a colorless liquid having a boiling point of 90°–91° C. (1 mm Hg).

EXAMPLE 6

Preparation of 2,2,4,5,5-pentamethyl-3-methylol-pyrrolidine. 20 g of 2,2,4,5,5-pentamethyl-3-formyl-pyrroline prepared as in example 4 were dissolved in 40 cc of $CH_3OH$ and placed in a flask fitted with a stirrer and dropping funnel.

A solution consisting of 50 cc of $H_2O$, 10 g of NaOH and 2 g of $NaBH_4$ was then slowly added to this solution through the funnel. The reaction mixture was kept at ambient temperature for three hours, after which the excess of $NaBH_4$ was destroyed with dilute HCl, the mixture was again alkalized with NaOH, and was extracted with ether.

The organic layer was dried and evaporated, and the said product was recovered with a yield of 90%.

After recrystallizing from petroleum ether, a white solid was obtained having a melting point of 90°–91° C., its structure being confirmed by IR, NMR and Mass analysis.

EXAMPLE 7

210 cc of 96% $H_2SO_4$, d.1.8, 140 cc of $H_2O$ and 50 g of di-tert-propargyl-amine were placed at ambient temperature in a 1 liter flask.

After the addition, the reaction mixture was heated to 125°–30° C. for about one and a half hours, during which time the reaction kinetics were followed by a gas chromatograph.

The reaction mixture was then cooled, poured over ice, alkalized and extracted three times with ether.

The combined ether extracts were dried and evaporated.

The residual solid was crystallized twice from petroleum ether (fraction 40°–60° C.) to give a white crystalline solid of M.P. 69°–71° C., which on IR, NMR and Mass examination was found to be 2,2,4,5,5-pentamethyl-3-formyl-$\Delta^3$-pyrroline.

EXAMPLE 8

Preparation of 2,2,2,4,5,5-pentamethyl-3-formyl-$\Delta^3$-pyrroline. 130 g of di-tert-propargyl-amine were added under stirring to a solution of 200 cc of 97% $H_2SO_4$, d.1.84, and 60 cc of $H_2O$ ($H_2SO_4$ concentration 83%) cooled to a temperature of −5° C. After the addition, the temperature of the reaction mass was rapidly raised to 130°–135° C.

After about one hour, the reaction mixture was cooled, poured over 400 g of crushed ice and alkalized with a 40% NaOH solution, taking care to keep the mixture temperature below ambient. The organic product was extracted with three 70 cc portions of toluene, the organic extracts were combined and concentrated by removing about 100 cc of solvent under vacuum.

The residue was cooled (0°–5° C.), and the said product was recovered as a crystalline solid.

By this method, 90 g of product were obtained, equal to a molar yield of about 61% calculated on the starting substance.

Note: The H₂SO₄ concentration can vary from 75 to 85%. The yield can vary from 50 to 75%.

In a similar manner, if a di-tert-propargyl-amine of the formula:

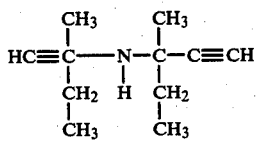

is reacted as indicated in Example 1, there is obtained a good yield of 2,4,5-trimethyl-2,5-diethyl-3-formyl-Δ³-pyrroline.

As indicated, the compounds of the present invention are useful for the preparation of anti-UV additives. When said compounds are reduced to the corresponding pyrrolidine, as in Example 6, and further reduced as in Example 7, the resulting 3-methylol compound can be reacted with 1,4-diacetoxybutane to form compounds of the formula

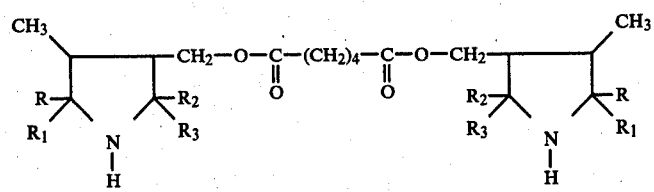

Said compounds have been found to be valuable for use as stabilizing agents against the action of UV-radiations on plastics materials, such as polyolefins, especially polyethylene and polypropylene.

We claim:

1. The compound, 2,2,4,5,5-pentamethyl-3-formyl-Δ³-pyrroline.

2. A process for the preparation of the compound of claim 1 which comprises reacting di-tert-propargylamine at a pH equal to or less than 3 in an environment comprising from 60 to 65% of sulfuric acid, based on the total solution, at a temperature of between 120° and 135° C.

3. A process for the preparation of the compound of claim 1 which comprises reacting di-tert-propargylamine at a pH equal to or less than 3 in an environment comprising between 45 and 50% of sulfuric acid and between 0.6 and 0.7% of mercury oxide, based on the total solution, at a temperature between 100° and 115° C.

* * * * *